(12) United States Patent
Helland

(10) Patent No.: US 6,203,548 B1
(45) Date of Patent: Mar. 20, 2001

(54) DISTRACTION APPARATUS

(75) Inventor: Per Helland, Paradis (NO)

(73) Assignee: Prototech AS, Fantoft (NO)

( * ) Notice: Subject to any disclaimer, the term of this patent is extended or adjusted under 35 U.S.C. 154(b) by 0 days.

(21) Appl. No.: 09/462,589

(22) PCT Filed: Jul. 7, 1998

(86) PCT No.: PCT/NO98/00205

§ 371 Date: Jan. 7, 2000

§ 102(e) Date: Jan. 7, 2000

(87) PCT Pub. No.: WO99/02097

PCT Pub. Date: Jan. 21, 1999

(30) Foreign Application Priority Data

Jul. 19, 1999 (NO) ................................................ 19973142

(51) Int. Cl.⁷ .................................................... A61F 2/36
(52) U.S. Cl. .............................. 606/105; 606/54; 606/59; 606/57; 606/53
(58) Field of Search .................................. 606/53, 54, 57, 606/58, 59, 60, 70, 71, 79, 80, 82, 86, 88, 87, 96, 97, 98, 102, 104, 105

(56) References Cited

U.S. PATENT DOCUMENTS

| | | | | |
|---|---|---|---|---|
| 2,391,537 | * | 12/1945 | Anderson | 606/105 |
| 5,074,865 | * | 12/1991 | Fahmy | 606/54 |
| 5,437,666 | * | 8/1995 | Tepic et al. | 606/54 |
| 5,941,877 | * | 8/1999 | Viegas et al. | 606/54 |
| 6,007,534 | * | 12/1999 | Gonzalez et al. | 606/54 |
| 6,010,501 | * | 1/2000 | Raskin et al. | 606/54 |

\* cited by examiner

*Primary Examiner*—Pedro Philogene
(74) *Attorney, Agent, or Firm*—Abelman, Frayne & Schwab

(57) ABSTRACT

The invention relates to a distraction apparatus for holding a fracture during the healing process. The apparatus includes screws or pins for insertion into a bone at points proximal and distal relative to a fracture site, and a pair of springs which can be connected externally between the screws or pins at spaced positions thereon. The springs act as an extension spring and a compression spring respectively between the screws or pins. The invention is characterized in that the springs are connected at the spaced positions at such distances relative to the bone that the springs will exert moments of force in order to obtain a desired torque load at the fracture site.

8 Claims, 5 Drawing Sheets

DISTRACTION APPARATUS

FIELD OF THE INVENTION

The invention relates to a distraction apparatus for holding a fracture during the healing process, comprising screws or pins for insertion into a bone at points proximal and distal relative to a fracture site, and a pair of springs which can be connected externally between the screws or pins at spaced positions thereon, which springs act respectively as a compression spring and an extension spring between the screws or pins.

BACKGROUND OF THE INVENTION

The invention has been developed especially in connection with the problems that are encountered in cases of fractures of the wrist or lowermost in the radius, one of the bones of the forearm, a very common fracture. Usually, fairly good results are achieved with plaster treatment, but it is known that in 10–20% of cases this results in an unacceptable malalignment or malunion, especially foreshortening. If there is presumed to be a danger of such malalignment or malunion, it is known to use external fixation. Transcutaneous screws are then screwed into the radius above the fracture and into the second metacarpal bone, and the alignment is locked by means of lockable universal joints, rods etc. At least two screws are used in each bone. When this technique is employed, the fracture lowermost in the radius is fixed indirectly because both the wrist joint and the joints in the campus are between the bones which are fixed with the screws. Despite this, this known method has proven to be adequate, and healing with a good alignment is usually achieved. However, the joints become stiff, and osteoporosis is a common complication. This causes considerable problems of rehabilitation and often a lasting reduction of mobility in wrist and finger joints, and there is therefore a certain degree of scepticism with respect to this method in the medical profession.

The drawbacks outlined above can be avoided if a distraction apparatus or fixator is used which permits the patient to move the joints during treatment.

Various fixators or distraction apparatus are known which seek to achieve this. For instance, No. 170 513 makes known an external bone fixation device which consists of fixation rods connected to bone fixation pins capable of being inserted into the bone, and an articulation part which joins the two rods. This known fixation device enables the patient to carry out some mobility exercises with the broken joint. DE 43 13 767 makes known a fixation device which includes a hinge member allowing limited joint movements.

U.S. Pat. No. 4,628,919 makes known an external fixation device which includes two articulatedly connected rods, attached to respective bone pins. This known device allows a certain freedom of movement in the wrist joint.

U.S. Pat. No. 5,437,666 makes known an external fixation device for osteosynthesis, which device includes bone fixation pins and connecting rods having a central disk articulation, and the device enables motion of the wrist joint about three axes.

Similarly, U.S. Pat. No. 5,437,667 makes known a fixation device for a distal fracture of the radius. Here too, a hinge mechanism is used which allows motion that does not differ from the normal kinematic motion of the wrist.

U.S. Pat. No. 5,047,865 makes known a distraction device where two bone fixation pins are interconnected by means of two springs which act as a compression spring and an extension spring, respectively. The device is especially intended for intra-articular fracture dislocations of fingers.

SUMMARY

In the case of fractures of the wrist it is correct to apply tractive forces to fractures, but it has been found that it is also very important to be able to provide the right moments at the wrist fracture.

One of the objects of the invention is thus to provide a distraction apparatus or fixator which makes it possible to balance the relation between choice of spring forces and distances for mounting points so that aligning moments are obtained at the fracture. Such aligning moments will help in the enhanced alignment and healing of the fracture site.

According to the invention, an apparatus is therefore proposed as mentioned in the introduction, which apparatus is characterised in that the springs are spring force adjustable and are connected in fixed receiving members in a respective frame part which carries the screws or pins, wherein the compression spring closest to the fracture site when the apparatus is in use is inclined relative to the exterior extension spring and the underlying bone so that the compression spring closest to the fracture site when the apparatus is in use is connected at a greater distance from the bone proximally than distally, reckoned along the screws or pins.

Although the new apparatus is intended primarily for fractures of the wrist where the type of fracture is of a nature such that it is desirable to use moments in addition to tractive force from the springs, the invention can of course also be used for other fractures wherever the apparatus might be suitable.

In each frame it is advantageous to construct a socket-type receiving member for the compression spring and insertion-type receiving member for the extension spring.

According to one variant, in each frame part there may advantageously be a socket-type receiving member for the compression spring and a hook-type receiving member for the extension spring.

When a hook-type receiving member is provided for the compression spring, this may be secured to or made as an integral part of a cylindrical body arranged slidably in a bore in the respective frame part, the cylindrical body having a keyhole-like cross-bore for interaction with a narrowed portion on a pin or screw.

The cylindrical body may be spring-loaded in the bore.

Each frame may advantageously have a bore with associated stud for securing interaction with a screw or pin.

An especially practical embodiment of the apparatus according to the invention would be one where the compression spring comprises a coil spring fixed in a surrounding split sleeve housing, wherein a first housing part is made in the form of a bottom sleeve wherein an outer bottom end is designed for connection of one end of the spring, and a second housing part, telescopic relative to the first housing part, is made in the form of a nut sleeve in threaded interaction with a threaded portion on a rod whose end is designed for connection.

In a practical embodiment of this kind, the extension spring may advantageously comprise a coil spring fixed in a surrounding split sleeve housing wherein a first housing part is made in the form of a bottom sleeve wherein an outer bottom part is designed for connection of one end of the spring, and a second housing part, telescopic relative to the first housing part, is made in the form of a bottom sleeve wherein an outer bottom part is designed for connection of the other end of the spring and a nut body is screwed onto the second housing part, which nut body has a pin which projects in through a slot in the second housing part and is secured to the attached coil spring end.

BRIEF DESCRIPTION OF THE DRAWINGS

The invention will now be explained in detail with reference to the drawings which show an exemplary embodiment, and wherein.

DETAILED DESCRIPTION OF THE INVENTION

Figure 1:
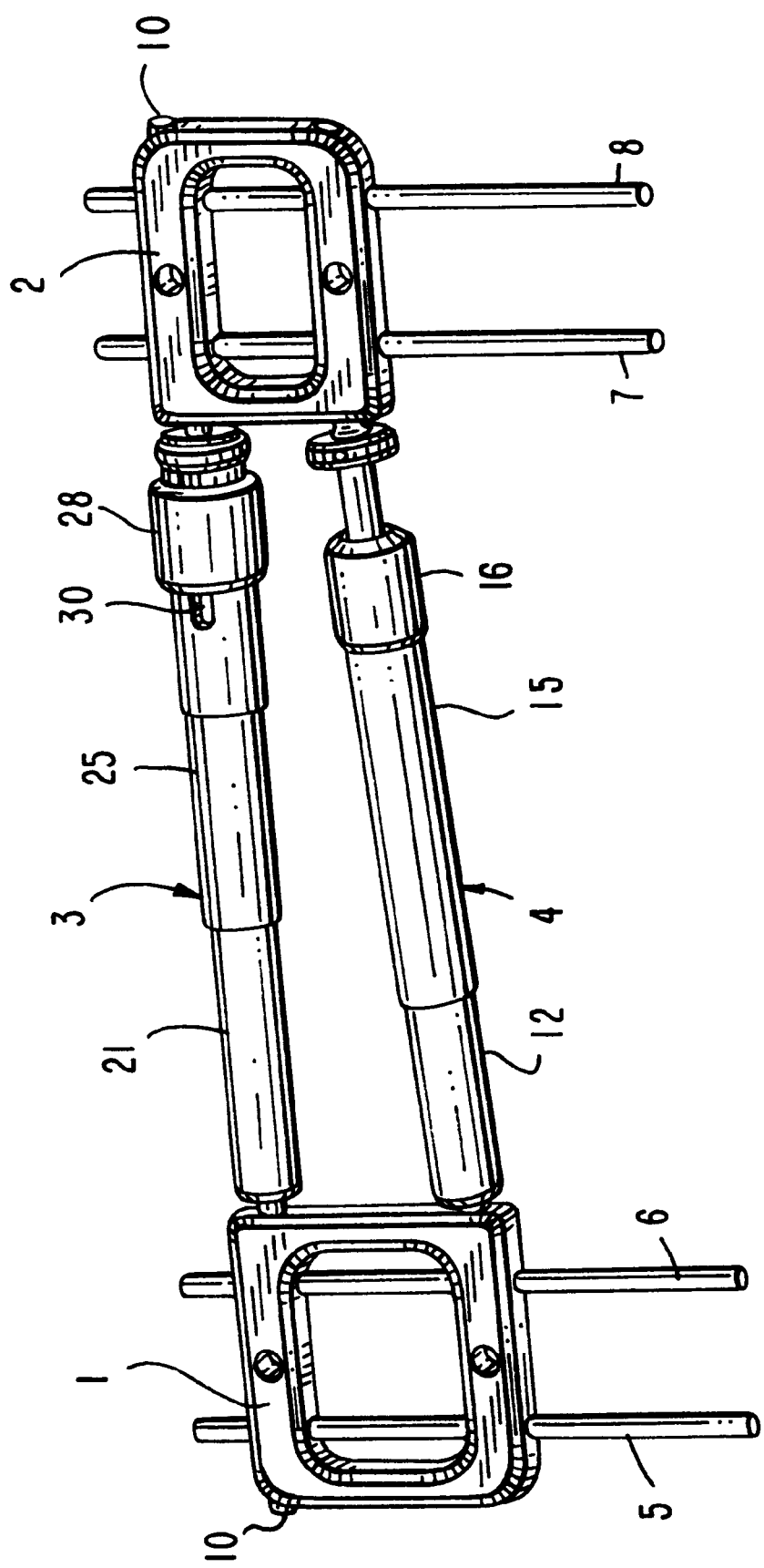
FIG. 1 shows an apparatus according to the invention.
Figure 2:
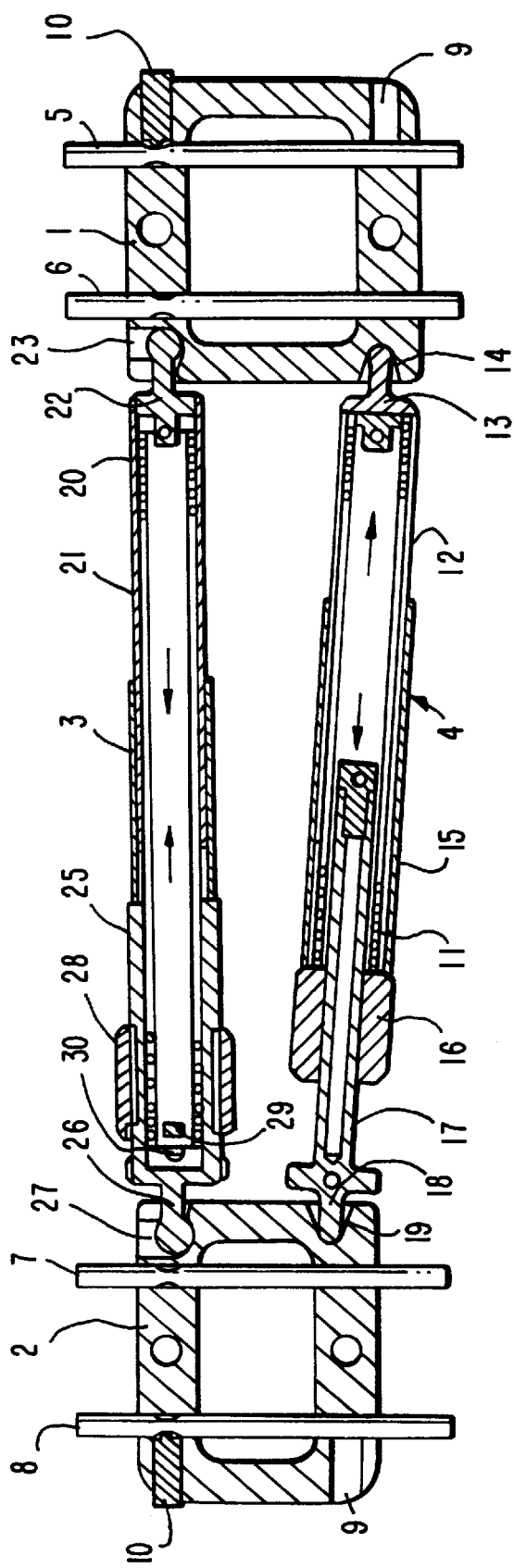
FIG. 2 shows a section through the apparatus in FIG. 1, the apparatus being turned relative to the position in FIG. 1.
Figure 3:
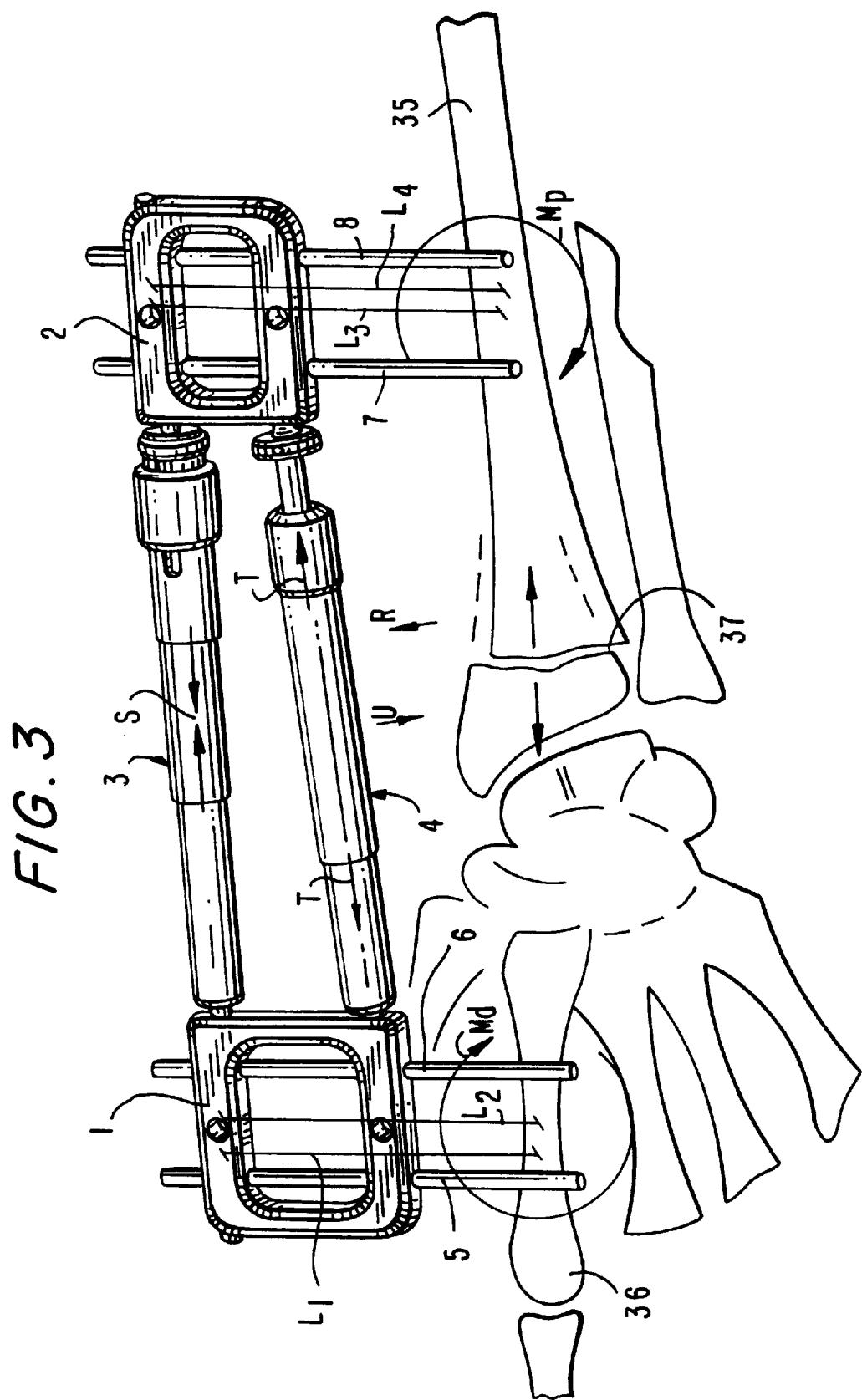
FIG. 3 shows the apparatus when mounted in connection with a distal fracture of the radius.

The apparatus shown in FIG. 1 includes a frame body 1, a slightly smaller second frame body 2 and spring mechanisms 3 and 4 arranged between said frame bodies. The frame bodies 1, 2 have bores for receiving pins 5, 6, and 7, 8, respectively, see also FIG. 2. These pins 5-8 are intended to be driven into the bones as shown in FIG. 3. As shown in particular in FIG. 2, each frame body 1, 2 has at least one bore 9 for receiving a stud 10 which serves to secure a respective pin, in the exemplary embodiment the pins 5 and 8.

The spring mechanism 4 acts as a compression spring whilst the spring mechanism 3 acts as an extension spring. The two spring mechanisms 3 and 4 are spring force adjustable. Thus, the compression spring mechanism 4 consists of a coil spring 11 which is arranged in a surrounding split sleeve housing. The split sleeve housing consists of a first housing part 12 made in the form of a bottom sleeve wherein the bottom end 13 is designed for connection to the frame part 1. In the frame part 1 there is constructed a socket-type receiving member 14 for the projecting, pin-like bottom part 13 of the housing part 12. The second housing part 15 of the split sleeve housing is made in the form of a nut sleeve, having a nut body 16 which has threaded interaction with a threaded portion of a rod 17, one end 18 of which is made in the form of a pin and rests in a recess 19 in the frame body 2. By screwing the nut sleeve 15, 16 backwards and forwards on the rod 17, the force of the compression spring can be varied.

The extension spring in the exemplary embodiment is also made in the form of a coil spring 20 which is fixed in a surrounding split sleeve housing wherein a first housing part 21 is made in the form of a bottom sleeve wherein an outer part 22 is made in the form of a pin which rests in an insertion-type receiving member 23 in the frame part 1. The spring 20 is fixed at 22 in the housing part 21. A second housing part 25 is also made in the form of a bottom sleeve wherein an outer bottom part 26 is made in the form of a pin which is placed inside an insertion-type receiving member 27 in the frame part 2. This second housing part 25 has an outer threaded portion on which there is screwed a nut body 28, which by means of a pin 29 projects through a slot 30 in the housing part 25 and interacts with the attached end of the coil spring 20. By screwing the nut body 28 backwards and forwards on the housing part 25, the force of the extension spring can be altered.

FIG. 3 shows the apparatus according to the invention used for a typical fracture of the wrist. The pins 7, 8 are driven into the radius 35 whilst the pins 5, 6 are driven into the metacarpal bone 36. The fracture is in the radius 35 and is indicated by means of the reference numeral 37. As will be appreciated, the apparatus applies tractive forces at the fracture. In addition it provides aligning moments of force MP and MD. These aligning moments of force will cause the site of fracture 37 to be aligned.

Figure 4:
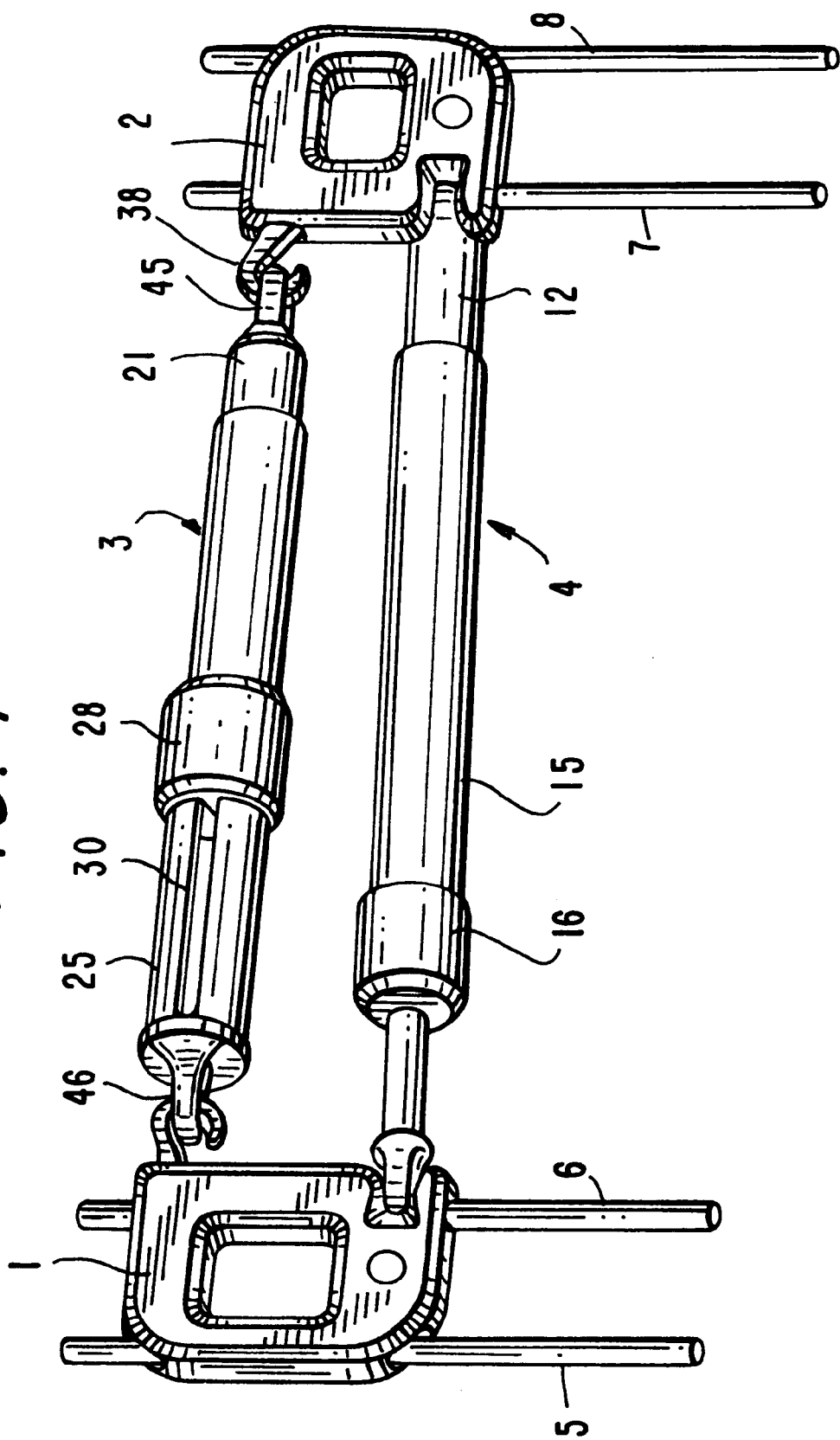
FIG. 4 shows a modified apparatus according to the invention.
Figure 5:
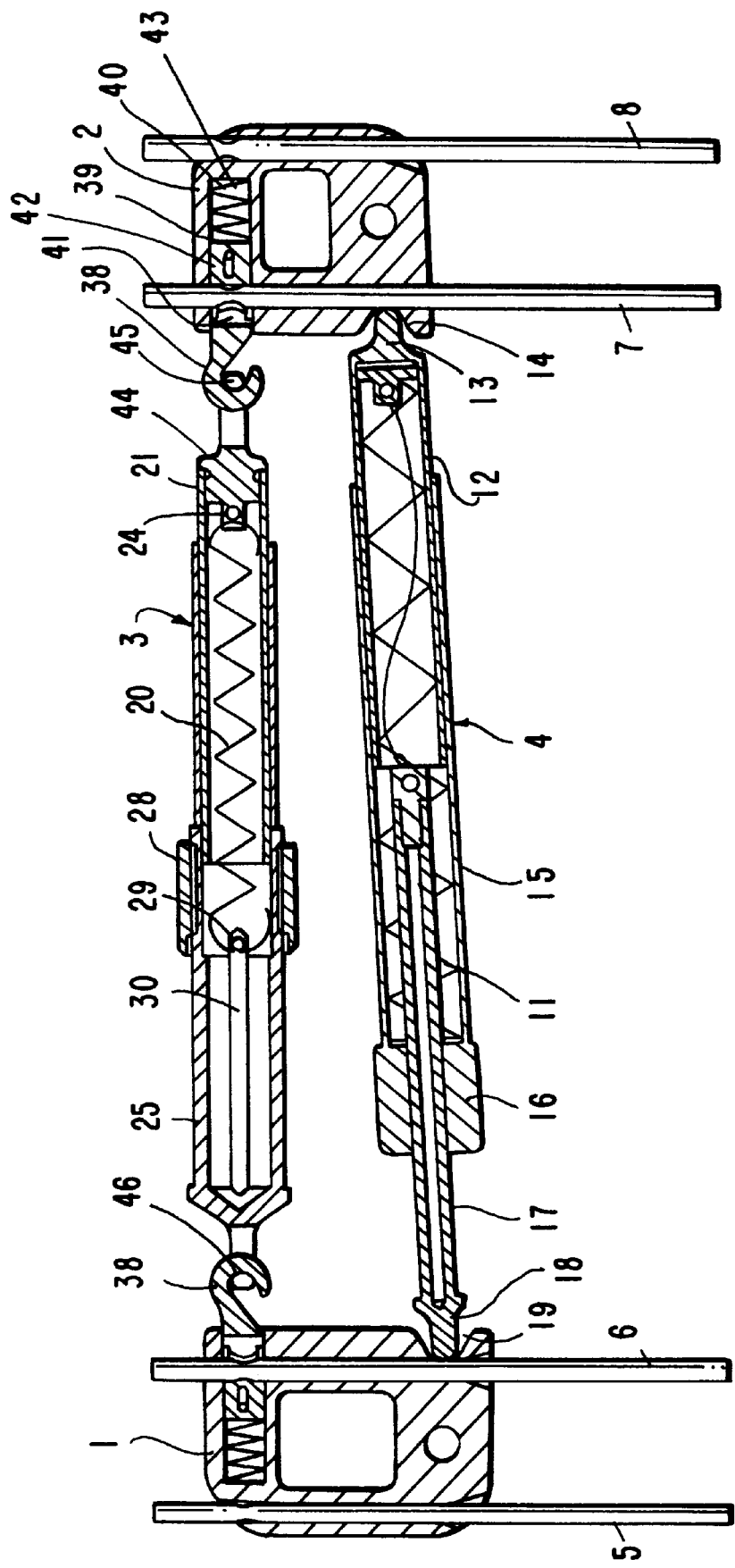
FIG. 5 shows a section through the apparatus in FIG. 4.

The apparatus in FIGS. 4 and 5 differs essentially from the apparatus described above in that a hook-type receiving member 38 is provided for the extension spring 3. Each hook-type receiving member of this kind includes a cylindrical body 39 slidably arranged in a bore 40 in the respective frame part 1, 2. In the cylindrical body 39 there is a keyhole-like cross-bore 41 for a pin 6 or 7. The pin 6, 7 has a narrowed portion 42 which is adapted to the keyhole-like opening 41. The cylindrical body 39 is spring-loaded by means of a spring 43 in the bore 40. For interaction with the respective hook 38, the first housing part 21 is provided with an outer part 44 formed to have a hook 45. Similarly, the end of the housing part 25 is formed to have a hook 46. When the extension spring 3 is connected, the respective pins 6, 7 will be locked in the respective frame part 1, 2.

The moments arise at an observation of moment distally and proximally. The moment distally is seen to be equal to the spring force $S \times l_1$ minus the spring force $T \times l_2$, and the moment proximally is seen to be equal to the spring force $T \times l_3$ minus the spring force $S \times l_1$.

Spring forces and distances are chosen so that a scissor effect is obtained at the fracture, which is favourable for this type of fracture.

The fixator is dynamic, thereby allowing movement of the wrist during the healing process of the fracture, which is positive for the desired healing.

In the case of the illustrated exemplary embodiment a desired tractive force is 2 kg in the fracture. In order to obtain a 2 kg traction in fractures, the compression spring 4 may, for example, be set at 4 kg and the extension spring 3 set at 2 kg, as a starting point. Since the spring mechanisms are adjustable, the spring force can be varied, for example, between 2.5 and 4 kg for the compression spring and 1.3 to 2 kg for the extension spring. The spring force in the compression spring is thus greater than in the extension spring.

In the exemplary embodiment, there is a different arm length for the compression spring distally and proximally. A positive rotational direction is obtained for the phalanx distally and the radius proximally, and thus forces U and R are obtained in their respective directions. This has a medical basis according to fracture research of fractures of the wrist.

Of course, it is also possible to change the arm of the extension spring as this will also cause a change of moment.

In the exemplary embodiment the proximal end of the apparatus is the end which has least moment-arm difference. Naturally, it is possible to turn the apparatus, but in practice this will be of little interest, as fracture displacement will virtually never be opposite that shown in FIG. 3.

What is claimed is:

1. A distraction apparatus for holding a fracture during healing, including screws or pins (5–8) for insertion into a bone at points proximal and distal relative to a fracture site, and a pair of springs (3, 4) which can be connected between the screws or pins (5–8) at spaced positions thereon, which springs (3, 4) act as an extension spring and a compression spring respectively between the screws or pins (5–8), characterised in that the apparatus comprises a distal and a proximal frame element (2, 1) carrying the screws/pins (5–8), two adjustable coil springs (3, 4), each frame element (2, 1) having fixed receiving members for the ends of coil springs (3, 4), said coil springs (3, 4) being received in and coupled to the receiving members and thereby to the frame elements (2, 1), the coil spring (4) closer to the bone when the apparatus is in use being the compression spring and being inclined relative to the bone and the other spring (3) in such a way that the compression spring (4) will have a greater distance from the bone proximally than distally, measured along the screws/pins (5–8), whereby aligning moments are created in the bone fracture.

2. A distraction apparatus according to claim 1, characterised in that in each frame part (1, 2) there are socket-type receiving members (14, 19) for the compression spring (4) and insertion-type receiving members (23, 27) for the extension spring (3).

3. A distraction apparatus according to claim 1, characterised in that in each frame part (1, 2) there is a socket-type receiving member (14, 19) for the compression spring (4) and hook-type receiving member (38) for the extension spring (3).

4. A distraction apparatus according to claim 3, characterised in that the hook-type receiving member (38) for the extension spring (3) is secured to or made as an integral part of a cylindrical body (39) arranged in a bore (40) in the respective frame part (1, 2), which cylindrical body (39) is displaceably arranged in the bore (40) and has a keyhole-like cross-bore (41) for interaction with a narrowed portion (42) of a pin or screw (5–8).

5. A distraction apparatus according to claim 4, characterised in that the cylindrical body (39) is spring-loaded (43) in the bore (40).

6. A distraction apparatus according to claim 1, characterised in that each frame part (1,2) has a bore (9) having associated stud (10) for securing interaction with a screw or pin (5–8).

7. A distraction apparatus according to claim 1, characterised in that the compression spring (4) comprises a coil spring (11) fixed in a surrounding span sleeve wherein a first sleeve part (12) is made in the form of a sleeve having a bottom end (13) connected to the end of the spring and a second sleeve part (15), telescopic relative to the first sleeve part (12), is made in the form of a nut sleeve in threaded interaction (16) with a threaded portion on a rod (17), one end of which rod (17) being connected to the other end of the spring.

8. A distraction apparatus according to claim 1, characterised in that the extension spring (3) comprises a coil spring (20) fixed inside a surrounding span sleeve wherein a first sleeve part (21) is made in the form of a sleeve having a bottom part (22) connected to one end of the spring and a second sleeve part (25), telescopic relative to the first sleeve part (21), is made in the form of a sleeve having a bottom part (26), whereby there on said second sleeve part (25) is screwed in place a nut body (28), which nut body has a pin (29) which projects in through a slot (30) in the said second sleeve part (25) and is connected to the attached coil spring end.

* * * * *